United States Patent [19]

Heitz et al.

[11] Patent Number: 5,313,001
[45] Date of Patent: May 17, 1994

[54] PROCESS FOR THE PREPARATION OF α-FLUROSTYRENE

[75] Inventors: Walter Heitz, Kirchhain; Arno Knebelkamp, Marburg, both of Fed. Rep. of Germany

[73] Assignee: Hoechst Aktiengesellschaft, Frankfurt am Main, Fed. Rep. of Germany

[21] Appl. No.: 927,430
[22] PCT Filed: Apr. 24, 1991
[86] PCT No.: PCT/EP91/00789
  § 371 Date: Nov. 17, 1992
  § 102(e) Date: Nov. 17, 1992
[87] PCT Pub. No.: WO91/16286
  PCT Pub. Date: Oct. 31, 1991

[30] Foreign Application Priority Data

Apr. 26, 1990 [DE] Fed. Rep. of Germany ....... 4013305

[51] Int. Cl.$^5$ ...................... C07C 43/02; C07C 22/00
[52] U.S. Cl. .................... 568/655; 570/143; 546/180; 546/346; 564/442
[58] Field of Search ............ 570/143; 568/655; 564/442; 546/346, 180

[56] References Cited

U.S. PATENT DOCUMENTS 2,752,400  6/1956  Prober .

OTHER PUBLICATIONS

*Patent Abstracts of Japan* 8, No. 7 (1984) 58–174 335.
*Patent Abstracts of Japan* 7, No. 242 (1983) 58–131 921.
Matsuda et al., *J. Org. Chem.* 27 (1962) 4015–20.
Heckes et al., *Synthesis* (1978) 217–220.
Heck, R. F., *Organic Reactions* 27 (1982) 345–90.
Heinze et al., *J. Fluorine Chem.* 31 (1986) 115–119.
Walter et al., *Chem. Abstracts* 114 (1991) 186116t.

*Primary Examiner*—Alan Siegel
*Attorney, Agent, or Firm*—Curtis, Morris & Safford

[57] ABSTRACT

Process for the preparation of α-fluorostyrene from fluoroolefins:

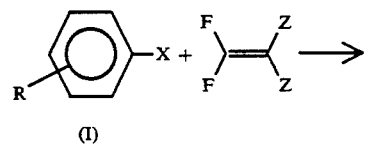

(I)

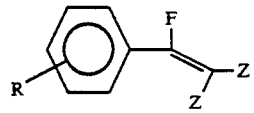

Z = hydrogen, fluorine, chlorine
X = iodine, bromine, chlorine.

A halogenated aromatic (I) is reacted with a fluorine-substituted ethylene (II) in the presence of a palladium catalyst to give an α-fluorostyrene (III), it being possible for R to be a hydrogen atom, a halogen atom, a $C_1$–$C_4$-alkyl group, a $C_1$–$C_5$-alkoxy group, an amino, alkylamino or dialkylamino group, an aryl radical or a fused aryl or heteroaryl ring, a hydroxyl or hydroxyalkyl group, a trifluoromethyl or perfluoroalkyl group or a nitro group.

10 Claims, No Drawings

PROCESS FOR THE PREPARATION OF α-FLUROSTYRENE

The present invention relates to a process for the preparation of α-fluorostyrenes by reaction of halogenated aromatics with fluoroolefins in the presence of a palladium catalyst.

Processes for the preparation of α-fluorostyrenes are known in the state of the art.

Thus the synthesis of α-fluorostyrene was described for the first time in 1962 by Matsuda et al. (K. Matsudo, J. A. Sedlak, J. J. Noland, G. C. Gleckler, J. Org. Chem. 27, 4015 (1962)), who reacted phenylacetylene or α-chlorostyrene with hydrofluoric acid. α,α-Difluoroethylbenzene is formed in the first stage and α-fluorostyrene can be obtained therefrom by pyrolysis at 400° C. The yields are very low in this reaction, it being possible to isolate 20% of α-fluorostyrene in the most favorable cases.

Higher yields of α-fluorostyrene can be obtained by reaction of bromine fluoride with styrene (L. Heckes, M. Hanack, Synthesis, 217, 1978). In this process, bromine fluoride is produced in situ and added on to styrene and, in a second step, α-fluorostyrene is formed in 63% yield with the elimination of hydrogen bromide. The addition of bromine fluoride on to substituted olefins takes place with high regioselectivity here. Because of its high reactivity and instability, bromine fluoride cannot be used directly for the synthesis but has to be produced in situ, e.g. from N-bromoacetamide and hydrogen fluoride in absolute ether. A further disadvantage is the generally difficult manipulability and toxicity of interhalogen compounds.

Palladium-catalyzed coupling reactions of fluorovinyl zinc compounds with aryl iodides were described in 1986 by Heinze and Burton (P. L. Heinze, D. J. Burton, J. Fluorine Chemistry 31 (1986) 1, 115).

The reaction of bromo- or iodo-trifluoroethene with zinc by this method yields a mixture of trifluorovinyl zinc bromide or iodide and bistrifluorovinylzinc, which react with aryl iodides under palladium catalysis to give styrene derivatives.

The yields which can be achieved are up to max. 74% in this two-stage reaction.

The object of the present invention was therefore to develop a process for the preparation of α-fluorostyrenes which can be carried out in a simple and uncomplicated manner, in which the starting materials can be conveniently manipulated and which is characterized by a high purity of the end products and by good yields.

The invention thus relates to a process for the preparation of α-fluorostyrenes by reaction of halogenated aromatics with fluoroolefins in the presence of a palladium catalyst, via a one-stage reaction, which is distinguished by good yields and the formation of very small amounts of by-products and also in that it is carried out rapidly and in an uncomplicated manner. In the process according to the invention, halogenated aromatics, preferably bromoaryl or iodoaryl compounds, are added on to fluoroolefins, under palladium catalysis, in a water-miscible organic solvent. Bases can be added to the reaction mixture here, secondary or tertiary amines preferably being used and the reaction being carried out at a temperature of between 50° and 180° C.

The reaction product is separated off by subsequent vacuum distillation and has purities of more than 95% with preparative yields of 30 to 80%. The GC yields are 50 to 90%.

The process according to the invention is characterized in that a halogen-substituted aromatic (I), preferably a bromine- or iodine-substituted aromatic, are (sic) reacted with a fluorine-substituted ethylene (II) in the presence of a palladium catalyst to give an α-fluorostyrene. The halogenated aromatic can be substituted in the ortho, meta or para position, especially in the meta or para position, the radical R being a hydrogen atom, a halogen atom, a $C_1$–$C_4$-alkyl group, a $C_1$–$C_5$-alkoxy group, an amino, alkylamino or dialkyl amino group, an aryl radical or a fused aryl or hetero aryl ring, a hydroxyl or hydroxyalkyl group, a tri fluoromethyl or perfluoroalkyl group or a nitro group.

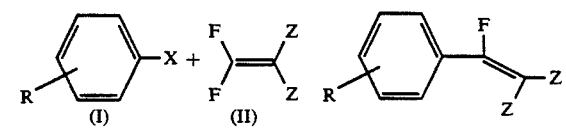

X = halogen, especially bromine or iodine
Z = hydrogen, fluorine, chlorine.

Possible catalyst systems for the process according to the invention are preferably palladium, palladium acetate, palladium chloride or triarylphosphine/palladium complexes.

Suitable reaction media are polar organic solvents, especially acetonitrile, dimethylformamide, methanol and dioxane, to which it is also possible to add so-called cocatalysts as well as the palladium catalyst. Phosphane or tri-o-tolylphosphane is preferably used as the cocatalyst in this process.

Suitable reaction temperatures for this process are in the range from 50° to 180° C., preferably in the range from 100° to 130° C. The α-fluorostyrenes prepared according to the invention can readily be polymerized to polymers with defined molecular weights, the degree of polymerization being strongly dependent on the initiator and amounts of initiator used.

On the basis of their refractive index, such fluoropolymers are used for example as sheathing materials for light waveguides or as similar materials on which high optical demands are made.

The palladium-catalyzed reaction of olefins with organic halides is known in the literature as the "Heck reaction" (R. F. Heck, J. Am. Chem. Soc. 90, 5518 (1968); R. F. Heck, Org. React. 27, 345 (1982)). The only organic halogen compounds which can be used are those which do not possess an $sp^3$-bonded hydrogen atom in the β-position relative to the halogen atom; otherwise these compounds undergo a β-H elimination under the conditions of the Heck reaction. Thus the reaction of bromoarenes with ethylene under palladium catalysis gave substituted styrenes and substituted stilbenes. A secondary reaction to the β-H elimination of the alkene in the Heck reaction is dehalogenation.

It has now been found, surprisingly, that in the reaction of halogenated aromatics with fluoroolefins, both the halogen atom on the aromatic and a fluorine atom on the olefin are cleaved, rather than the expected hydrogen atom of the olefin.

Thus e.g. in the reaction of bromobenzene with vinylidene fluoride, the unexpected α-fluorostyrene is found to be the main product while the expected reaction product, namely β,β-difluorostyrene, is formed in only very small amounts. Depending on the reaction conditions, biphenyl and stilbenes can also be formed. It has been found that this secondary reaction is strongly dependent on pressure, so that styrenes are preferentially formed at higher pressures (yields of up to 80%) while stilbenes are predominantly formed at lower pressures.

Bromoarenes or iodoarenes are preferably used as halogenated aromatics.

Both substituted and unsubstituted monocyclic or polycyclic aromatics and heteroaromatics, e.g. benzene, naphthalene, quinoline or pyridine, are suitable for the process according to the invention.

It has now been found, surprisingly, that donors as substituents on the halogenated aromatic increase the yields, whereas acceptors greatly reduce both the reaction rate and the yields. By contrast, the relationships are reversed in the Heck reaction.

In the process according to the invention, the aromatic is preferably substituted in the para position, meta substitution also being possible depending on the substituent; on the other hand, ortho substituents, especially bulky groups, have an adverse effect on the course of the reaction because of their steric hindrance.

Fluoroolefins which are suitable for the process according to the invention can be di-, tri- or tetra-substituted, it being necessary for two fluorine atoms to be located on the same carbon atom so that α-fluorostyrenes are formed as reaction products. If the olefins are only monosubstituted, styrenes are obtained because here too the fluorine atom on the olefin is cleaved. Thus styrene and stilbene are obtained from iodobenzene and vinyl fluoride. By contrast, β-fluorostyrenes are formed in the case of olefins which carry the halogen atoms on two different carbon atoms.

The yields of the process according to the invention can be further improved by addition of the olefin component in excess; an excess of 2.5 equivalents of olefin, for example, is preferred and larger excesses are particularly preferred. The excess olefin not consumed in the reaction can easily be recovered.

In industrial-scale processes, the unreacted olefin can be fed back continuously into the reactor by a cyclic procedure while the reaction product is separated from the reaction mixture. Such a process is particularly advantageous from both economic and ecological points of view.

The reaction is preferably carried out in a polar solvent, acetonitrile, dimethylformamide, methanol, dioxane and ethyl acetate, for example, being particularly preferred.

Secondary and tertiary amines are used as bases, trialkylamine being particularly preferred, but it also being possible to use inorganic acetates and carbonates. It is conventional to add for example 2.5 mol of base per mol of halogenated aromatic.

Examples of possible catalyst systems which are suitable for the claimed process are elemental palladium, palladium acetate, palladium chloride or triarylphosphine/palladium complexes, but it is also possible here to use all the catalysts or catalyst systems which are suitable for the Heck reaction; the concentrations should be between 0.01 and 10 mol %, advantageously between 1 and 2 mol %, of added catalyst.

The α-fluorostyrene obtained according to the invention is distinguished by a high purity, so expensive upstream purification processes, e.g. in subsequent polymerization processes to produce poly(α-fluorostyrene), can be dispensed with.

Fluoropolymers are distinguished by a special property profile which distinguishes them from other polymers and therefore makes them particularly interesting for research and technology.

Thus, for example, they have a high heat stability, a high resistance to weathering, a low affinity for moisture and a low flammability, are thermally and chemically very stable (sic) and possess special surface properties.

Like some other fluoropolymers, poly(α-fluorostyrene) has a low refractive index, which makes this compound particularly valuable for example for fields of application in which high demands are made on the optical properties of the materials used, such as core and sheathing materials of light waveguides, or for sectors of optical communication engineering, but also for resists. Applications in the field of space technology are likewise conceivable.

EXAMPLES

Preparation of α-fluorostyrene 18.37 g of iodobenzene (90 mmol), 0.20 g of palladium (II) acetate (0.9 mmol) and 23.78 ... (sic) of triethylamine (235 mmol) were weighed out successively into a 250 ml steel autoclave and dissolved in approx. 50 ml of acetonitrile. After the autoclave had been closed, it was degassed twice and 15.0 g of vinylidene fluoride (235 mmol) were condensed in.

The autoclave was heated to 115° C. in an oil bath, with vigorous stirring, and this temperature was maintained for 18 h.

After cooling to room temperature, the reaction solution was added to water. Extraction was carried out with diethyl ether. The ether phase was dried over sodium sulfate, filtered and concentrated on a rotary evaporator. The remaining highly volatile components were separated off by distillation at normal pressure. The main product was obtained by vacuum distillation as a clear colorless liquid boiling at 46° C./15 Torr.

Yield: 4.25 g (35 mmol)=39% of theory.
GC purity >99%.

Preparation of 4-methoxy-α-fluorostyrene 23.40 g of 4-iodoanisole (100 mmol), 0.45 g of palladium(II) acetate (2 mmol) and 25.47 g of triethylamine (250 mmol) were weighed out successively into a 250 ml steel autoclave and suspended in approx. 50 ml of dimethylformamide.

After the autoclave had been closed, it was degassed twice and 16.98 g of vinylidene fluoride (250 mmol) were condensed in. The autoclave was heated to 115° C. in an oil bath, with vigorous stirring, and this temperature was maintained for approx. 48 h. After cooling to room temperature, the reaction solution was added to 400 ml of 1% sodium hydroxide solution. Extraction was carried out with twice 200 ml of methylene chloride and the extract was dried over sodium sulfate, filtered and concentrated on a rotary evaporator. The main product, boiling at 55°–60° C./4–5 Torr, was obtained by fractional vacuum distillation (addition of 0.1 g of 2,6-di-tert-butylphenol as a stabilizer).

Yield: 9.37 g (60 mmol/60% of theory).
GC purity >95%.

Preparation of 4-phenyl-α-fluorostyrene 13.60 g of 4-iodobiphenyl (50 mmol), 0.12 g of palladium(II) acetate (0.5 mmol) and 12.62 g of triethylamine (125 mmol) were weighed out successively into a 250 ml steel autoclave and dissolved in 100 ml of dimethylformamide.

After the autoclave had been closed, it was degassed twice and 8.01 g of vinylidene fluoride were condensed in. The autoclave was heated to 115° C. in an oil bath, with vigorous stirring, and this temperature was maintained for approx. 18 h.

After cooling to room temperature, the reaction solution was added to 200 ml of 5% hydrochloric acid. Extraction was carried out with methylene chloride. The yield was found to be 70% by gas chromatography.

Preparation of 4-fluoro-α-fluorostyrene 22.01 g of 4-fluoroiodobenzene (100 mmol), 0.225 g of palladium(II) acetate (1 mmol) and 25.30 g of triethylamine (250 mmol) were weighed out successively into a 250 ml steel autoclave and dissolved in approx. 60 ml of N-methylcaprolactam.

After the autoclave had been closed, it was degassed twice and 16.00 g of vinylidene fluoride (250 mmol) were condensed in.

The autoclave was heated to 115° C. in an oil bath, with vigorous stirring, and this temperature was maintained for approx. 18 h. After cooling to room temperature, the reaction solution was added to 200 ml of 5% hydrochloric acid. Extraction was carried out with a diethyl ether/pentane mixture (1:1). The organic phase was dried over sodium sulfate, filtered and concentrated on a rotary evaporator.

The main product was obtained by vacuum distillation as a clear colorless liquid boiling at 52° C./28 Torr.

Yield: 4.57 g (33 mmol/33% of theory).
GC purity>99%.

Preparation of E-α,β-difluorostyrene 18.37 g of iodobenzene (90 mmol), 0.20 g of palladium (II) acetate (0.9 mmol) and 22.72 g of triethylamine (225 mmol) were weighed out successively into a 250 ml steel autoclave and dissolved in approx. 50 ml of acetonitrile.

After the autoclave had been closed, it was degassed twice and 18.45 g of trifluoroethylene (225 mmol) were condensed in.

The autoclave was heated to 115° C. in an oil bath, with vigorous stirring, and this temperature was maintained for approx. 18 h. After cooling to room temperature, the reaction solution was added to 200 ml of 5% hydrochloric acid and extracted twice with 200 ml of diethyl ether. The organic phase was dried over sodium sulfate, filtered and concentrated on a rotary evaporator. The yield is 69% as determined by gas chromatography. Vacuum distillation produced at 50° C./25 Torr 4.21 g of a fraction composed of E-α,β-difluorostyrene to the extent of 85% (GC).

We claim:

1. A process for the preparation of α-fluorostyrene from fluoroolefins:

Z=hydrogen, fluorine, chlorine
X=iodine, bromine, chlorine
characterized in that a halogenated aromatic (I) is reacted with a fluorine-substituted ethylene (II) in the presence of a palladium catalyst to give α-fluorostyrene (III), wherein R is a hydrogen atom, a halogen atom, a $C_1$-$C_4$-alkyl group, a $C_1$-$C_5$-alkoxy group, an amino, alkylamino or dialkylamino group, an aryl radical or a fused aryl or heteroaryl ring, a hydroxyl or hydroxyalkyl group, a trifluoromethyl or perfluoroalkyl group or a nitro group.

2. A process for the preparation of α-fluorostyrene according to claim 1, characterized in that the reaction is carried out in the presence of a base.

3. A process for the preparation of α-fluorostyrene according to claim 2, characterized in that the base used is a secondary or tertiary amine.

4. A process for the preparation of α-fluorostyrene according to claim 1, characterized in that the reaction is carried out in a polar solvent.

5. A process for the preparation of α-fluorostyrene according to claim 4, characterized in that the polar solvent used is acetonitrile, dimethylformamide, methanol, dioxane, or ethyl acetate.

6. A process for the preparation of α-fluorostyrene according to claim 1, characterized in that the halogenated aromatic used is substituted in the meta- ir para-position relative to the halogen atom X by a radical R.

7. A process for the preparation of α-fluorostyrene according to claim 1, characterized in that the reaction is carried out with the addition of co-catalysts.

8. A process for the preparation of α-fluorostyrene according to claim 7, characterized in that the co-catalyst used is a phosphane or tri-o-tolyl-phosphane.

9. A process for the preparation of α-fluorostyrene according to claim 1, characterized in that the reaction is carried out at a temperature of 50° to 180° C.

10. A process for the preparation of α- fluorostyrene according to claim 1, characterized in that the yields of α-fluorostyrenes are 50% to 90%.

* * * * *

UNITED STATES PATENT AND TRADEMARK OFFICE
CERTIFICATE OF CORRECTION

PATENT NO. : 5,313,001
DATED : May 17, 1994
INVENTOR(S) : Heitz et al.

It is certified that error appears in the above-identified patent and that said Letters Patent is hereby corrected as shown below:

Claim 6, Column 6, line 43, change "meta- ir para" to --meta- or para--.

Signed and Sealed this

Twentieth Day of September, 1994

Attest:

BRUCE LEHMAN

*Attesting Officer*         *Commissioner of Patents and Trademarks*